United States Patent
Buschmann et al.

(10) Patent No.: US 10,907,311 B2
(45) Date of Patent: Feb. 2, 2021

(54) METHOD AND ROAD FINISHER FOR DETECTING INTERFERING OBJECTS DURING THE CREATION OF A TEMPERATURE FIELD OF THE PAVING LAYER

(71) Applicant: JOSEPH VOEGELE AG, Ludwigshafen/Rhein (DE)

(72) Inventors: Martin Buschmann, Neustadt (DE); Henning Delius, Edenkoben (DE)

(73) Assignee: JOSEPH VOEGELE AG, Ludwigshafen/Rhein (DE)

( * ) Notice: Subject to any disclaimer, the term of this patent is extended or adjusted under 35 U.S.C. 154(b) by 24 days.

(21) Appl. No.: 16/516,696

(22) Filed: Jul. 19, 2019

(65) Prior Publication Data
US 2020/0025970 A1 Jan. 23, 2020

(30) Foreign Application Priority Data
Jul. 20, 2018 (EP) ..................................... 18184705

(51) Int. Cl.
*G01J 5/00* (2006.01)
*E01C 19/42* (2006.01)
(Continued)

(52) U.S. Cl.
CPC .............. *E01C 19/42* (2013.01); *B60Q 5/005* (2013.01); *B60Q 9/00* (2013.01); *G01V 9/005* (2013.01); *G01J 2005/0077* (2013.01)

(58) Field of Classification Search
CPC ........ E01C 19/42; E01C 19/48; G01J 5/0066; G01J 2005/0077
(Continued)

(56) References Cited

U.S. PATENT DOCUMENTS 6,749,364 B1 * 6/2004 Baker ................... E01C 19/288
404/118
9,540,778 B2 1/2017 Rutz et al.
(Continued)

FOREIGN PATENT DOCUMENTS

DE 10 2014 222 693 A1 5/2016
EP 2 666 908 A1 11/2013
(Continued)

OTHER PUBLICATIONS

European Search Report dated Nov. 19, 2018, Application No. 18184705.4, Applicant Joseph Voegele AG, 7 Pages.
(Continued)

*Primary Examiner* — Raymond W Addie
(74) *Attorney, Agent, or Firm* — Brooks Kushman P.C.

(57) ABSTRACT

A method and a road finisher for creating a temperature field of a newly laid paving layer corrected for interfering-related temperature measurement errors. It is recognised that when the paving layer is paved, a measuring point is covered by an interfering object at a first time if, contrary to an expected material-specific cooling at a later second time during paving at the same measuring point, a larger temperature value particularly lying within a nominal temperature range than a temperature value measured to the preceding first time is measured, wherein instead of the temperature value detected at the first time a new temperature value is assigned to the measuring point in the temperature field.

19 Claims, 5 Drawing Sheets (51) Int. Cl.
  *B60Q 5/00* (2006.01)
  *B60Q 9/00* (2006.01)
  *G01V 9/00* (2006.01)

(58) Field of Classification Search
  USPC .......................... 404/72, 75; 250/338.1, 342
  See application file for complete search history.

(56) References Cited

U.S. PATENT DOCUMENTS

| | | | |
|---|---|---|---|
| 9,587,361 B2* | 3/2017 | Oetken | ................. E02D 3/0265 |
| 10,184,838 B2* | 1/2019 | Becher | .................... E01C 19/48 |
| 10,655,283 B2 | 5/2020 | Andersson | |
| 10,662,595 B2* | 5/2020 | Buschmann | ............... E01C 7/00 |
| 10,669,678 B2* | 6/2020 | Marsolek | ............... E01C 19/288 |
| 2009/0142133 A1* | 6/2009 | Glee | ........................ E01C 19/48 |
| | | | 404/75 |
| 2014/0086684 A1* | 3/2014 | Sehr | ........................ G01J 5/047 |
| | | | 404/84.05 |
| 2016/0042235 A1 | 2/2016 | Buschmann et al. | |
| 2016/0060819 A1* | 3/2016 | Oetken | ................. E01C 19/004 |
| | | | 404/72 |
| 2016/0061755 A1 | 3/2016 | Delius et al. | |
| 2016/0131633 A1 | 5/2016 | Schoenbach et al. | |
| 2017/0322088 A1* | 11/2017 | Becher | .................... E01C 23/01 |
| 2019/0186084 A1 | 6/2019 | Marsolek | |

FOREIGN PATENT DOCUMENTS

| | | |
|---|---|---|
| EP | 2 789 741 A1 | 10/2014 |
| EP | 2 982 951 A1 | 2/2016 |
| EP | 2 990 531 A1 | 3/2016 |
| JP | 2005097958 A | 4/2005 |
| JP | 2016040445 A | 3/2016 |
| JP | 2016048024 A | 4/2016 |
| JP | 2016102396 A | 6/2016 |
| JP | 2017031797 A | 2/2017 |
| JP | 2018523035 A | 8/2018 |
| WO | 00/70150 A1 | 11/2000 |

OTHER PUBLICATIONS

Japanese Search Report dated Sep. 15, 2020 (with English Machine Translation), Application No. 2019-131834, 20 Pages.

Japanese Office Action dated Sep. 29, 2020 (with English Machine Translation), Application No. 2019-131834, 4 Pages.

\* cited by examiner

METHOD AND ROAD FINISHER FOR DETECTING INTERFERING OBJECTS DURING THE CREATION OF A TEMPERATURE FIELD OF THE PAVING LAYER

CROSS-REFERENCE TO RELATED APPLICATIONS

This application claims foreign priority benefits under 35 U.S.C. § 119(a)-(d) to European patent application number EP 18 184 705.4, filed Jul. 20, 2018, which is incorporated by reference in its entirety.

TECHNICAL FIELD

The disclosure refers to a method for creating a temperature field and to a road finisher.

BACKGROUND

The processing temperature of asphalt is an important process variable in asphalt road construction and has a considerable influence on the usage properties, in particular on the load capacity, the bond between the layers and the service life of the pavement laid. For this reason, measuring the paving temperature of newly laid road surfaces is becoming increasingly important. Meanwhile, it has also become common practice that government agencies increasingly require metrological verification of the paving temperatures.

The problem, however, is that during paving, incorrect measurements repeatedly occur when determining the temperature of the applied road surface, which are caused by interfering objects such as construction site personnel, rollers or measuring units, which are at least temporarily located in the measuring area behind the paving screed on the new road surface and thus conceal some of the measuring points of the temperature field behind the paving screed. If an image is then taken of the intrinsic temperature in the temperature field to be generated, the temperature field is falsified in this respect at least in places, because the intrinsic temperature of such temporary interfering objects is clearly outside an expected temperature range. Such a situation is therefore unsatisfactory, particularly for documentation purposes.

Up to now, various measuring systems have been used to measure the temperature of the newly laid road surface behind the paving screed of the road finisher, such as infrared scanners and reciprocating pyrometer units or a plurality of pyrometers (pyrometer arrays). Such devices can be used to generate a more or less closed temperature image in the form of a temperature profile of the laid paving layer.

A known system uses an infrared camera for this, whose image data is converted into scanning lines by software. The scanning lines have a defined distance from the rear edge of the screed. Each scanning line represents a transverse temperature curve of the laid layer.

To produce an image of the more homogeneous temperature field, i.e., without an image of individual cooling points, systems are also used in practice which are configured to overwrite intermediate non-nominal temperature measurements (cooling points) in a control process downstream of the actual temperature measurement process by means of interpolation of nominal temperature measurements. However, the disadvantage of this method, which is carried out by interpolation, is that it is also possible to overwrite measured values which are actually detected on too cold paving material and therefore not only temporarily positioned interfering objects on the paving layer can be detected and compensated in the temperature field.

WO 00/70150 A1 discloses a road finisher with a detection unit attached thereto for carrying out a temperature detection of the paving layer newly laid by the road finisher, wherein any detected cooling points are identified by means of a marking device of the road finisher for a compaction operation.

DE 10 2014 222 693 A1 discloses a road finisher with a device mounted thereon for determining the temperature of a road surfacing material, the device comprising an infrared temperature sensor which is pivotally arranged transversely to the direction of travel of the road finisher by means of a motor connected thereto.

EP 2 982 951 A1 discloses a road finisher with a thermographic module positioned on the roof, which is designed to detect a deviation area of the laid pavement if one or more deviation criteria are met based on temperature values detected for the area, wherein images, for example with respect to temporary interfering objects, can be assigned to the deviation area.

The EP 2 990 531 A1 discloses a system for road finishers with a temperature measuring device that can be used to determine the cooling behaviour of a pavement paved by a road finisher by repeatedly recording the temperature values of the pavement laid.

EP 2 666 908 A1 discloses a method for determining a material-specific cooling behaviour for material mixtures used in road construction.

EP 2 789 741 A1 discloses a road finisher with a thermographic device attached to it for detecting a temperature profile of at least one area of a layer laid behind the screed.

SUMMARY

In order to be able to better assess the actual quality of a paving layer on the basis of a temperature field along the paving path, or to improve electronic evaluation and/or further processing, there should be no, or at least negligibly few, erroneous measurements in the measuring range of the temperature field, in particular erroneous measurements which are integrated in the temperature field due to temporary interfering objects.

An object of the disclosure is to provide a method and a road finisher, which can be used to differentiate between actual material defects of the paving layer and specific faulty measurements with regard to interfering objects temporarily located on the new paving layer, so that a temperature field corrected for interfering object-related faulty measurements can be generated.

The disclosure refers to a method for creating a temperature field of at least one section of a paving layer laid by means of a paving screed of a road finisher, wherein an interfering object temporarily positioned on the laid paving layer within at least one measuring range of the temperature field predetermined thereon is detected, the intrinsic temperature of which is below a desired nominal value temperature for the measuring range, so that an image of the intrinsic temperature of the interfering object in the temperature field to be generated falsifies the same at least in places, a temperature of at least one measuring point lying within the measuring range being measured at different times in order to detect the interfering object.

In accordance with the disclosure, it is recognised that during the laying of the paving layer, the measuring point is covered by an interfering object at a first time if, contrary to an expected material-specific cooling at a later second time during the laying at the same measuring point a larger temperature value, in particular lying within the nominal temperature range is measured than a temperature value detected at the preceding time, wherein instead of the temperature value detected at the first time a new temperature value of the measuring point is assigned in the temperature field.

In the context of the disclosure, the temperature field refers to a two-dimensional temperature distribution on the basis of which each measuring point (room point) is assigned a temperature. In the temperature field, certain temperatures at the respective measuring points can be represented by certain colours. In the disclosure, the temperature field preferably forms a thermal image of the temperature distribution on the surface of the newly laid paving layer.

In accordance with the disclosure, a temperature gradient recorded for a measuring point thus refers to an interfering object at the measuring point in the temperature field, which was positioned there at least temporarily between the measuring period and thus prevented the actually intended temperature measurement on the cover material laid there. The temperature gradient provides a simple parameter for reliably detecting the presence of an interfering object.

Consequently, with the help of embodiments according to the disclosure, a paving temperature actually measured there can be assigned to each field point of the measuring range in the temperature field, even if the detection of the paving temperature there was temporarily hindered by an interfering object. In other words, embodiments according to the disclosure can be used to reliably filter out interfering object-related temperature values during the creation of the temperature field.

The detection of the temperature at the respective measuring points preferably takes place during paving at recurring measuring intervals. The measuring intervals can be controlled as a function of the paving speed, so that the temperature measurement can take place at the respective measuring points with sufficient repetitions in order to reliably detect interfering objects. The method according to the disclosure can thus continuously carry out temperature measurements at the respective measuring points, detect interfering objects and reliably filter them out during temperature field generation.

For example, a roller vehicle that follows the road finisher in order to compact the paving layer newly laid by the road finisher to a predetermined level can be considered as an interfering object that can be detected by means of the disclosure. In addition, measuring units, such as levelling instruments, can be positioned at least temporarily on the new road surface within the measuring range to interfere with the temperature field generation. Operating personnel can also be detected as an interference object if they are in the measuring range or interfere with the temperature field measurement when crossing the measuring range. Basically, all bodies which are not part of the new paving layer and which prevent direct temperature detection at the desired measuring point can be detected as interfering objects.

According to the disclosure, implausible interfering object-related measured values can be detected using simple method steps, in particular using technology already provided on the road finisher, on the basis of which a correction of the temperature field can be carried out in such a way that interfering object-related faulty measurements can be eliminated or at least greatly reduced, making the temperature field more meaningful overall, above all for quality control purposes.

In addition, the temperature field corrected by embodiments of the disclosure of faulty measurements related to the interfering object can be used better as a control input variable for control processes, for example for sequence controls of certain paving functions, on the road finisher itself and/or on other vehicles or equipment involved in paving, for example on material mixing plants, on material supply vehicles and/or on compaction vehicles, in order to optimally control the work processes carried out in this respect.

Finally, the method according to the disclosure offers the technical advantage that the temperature field, which has been corrected for faulty measurements related to interference objects, has a reduced data storage volume compared to known solutions, so that it can be better documented and further processed.

One variant of the disclosure provides the use of object recognition in an evaluation software to detect the interfering object. Preferably, the evaluation software checks whether objects move relative to the paving speed in order to detect the interfering object.

When creating the temperature field for the new paving layer, it is preferable to use the later higher temperature value recorded at the same measuring point as the new temperature value, so to speak as the correction value, for the measuring point. This can be done with the proviso that the larger temperature value is still within the or an adjusted nominal temperature range.

In terms of control technology, this can be achieved, for example, by overwriting the excessively cold temperature value measured at the first time of temperature measurement due to the presence of an interfering object by a control unit from the larger temperature value recorded later and actually present at the same measuring point. This can be carried out by means of a sequence control process, whereby the interfering object temperature at the measuring point remains set in the temperature field until a higher temperature for the measuring point is detected. As a result, it is possible that an intrinsic interfering object temperature which may initially have been incorrectly assigned to a measuring point due to the presence of an interfering object is subsequently replaced during paving by the actual paving temperature of the paving material at the measuring point, in particular by means of feedback control, so to speak at a later time a correction with regard to the new temperature value is carried out for the same measuring point.

The method can be better adapted to the actual paving situation by correcting the later larger temperature value detected at the same measuring point, taking into account a predetermined or determined cooling coefficient of at least one adjacent measuring point, before the new temperature value thus obtained replaces the temperature value detected at the first time. This allows a cooling at the measuring point to be taken into account, so that it does not matter how long the interfering object was positioned at the measuring point, because the cooling coefficient can be used to determine exactly how the actual temperature of the measuring point would actually have been at the preceding first time in the temperature field if the interfering object had not been positioned at the measuring point at that time.

One variant provides that the new temperature value is calculated, preferably as a function of the detected temperature gradient at the measuring point x, using a characteristic field.

One embodiment of the disclosure provides as a plausibility check that the temperature value detected at the first point in time is replaced by the new temperature value when the temperature value detected at the first time does not exceed a temperature threshold value when creating the temperature field for the paving layer. This ensures that only faulty measurements related to the interfering object and whose temperature values are below the temperature threshold can be corrected, i.e., not actual faulty measurements on the paving material of the paving layer that indicate paving material that has been installed too cold in places.

The use of the temperature threshold value makes it easy to clearly distinguish between procedurally interfering object-related faulty measurements and paving material-specific faulty measurements, i.e., cold spots in the paving layer, on the basis of which interfering object-related faulty measurements can be precisely filtered out in the temperature field. On the other hand, the temperature faulty measurements typically detected above the temperature threshold value, but not nominal, remain contained in the temperature field, so that the temperature field reliably indicates paving errors, i.e., indicates that the paving material has been installed too coldly in places along the laid paving layer. Preferably, the temperature threshold value can be adjusted as a function of an ambient temperature detected on the road finisher and/or a measurement time elapsed for the measuring point.

It is particularly practicable if respective temperature values of several measuring points are detected along at least one measuring line running transversely to or in the paving direction within the measuring range. Preferably, the resolution along the measuring line can be changed, so that a scanning accuracy can be adjusted in an advantageous way in view of different quality requirements.

A time-shifted temperature detection of respective measuring points is in particular possible by the fact that the at least one measuring line is moved at different times at least temporarily opposite to the paving direction during paving the paving layer for detecting the respective temperatures at measuring points arranged therein. While the road finisher is moving slowly in the paving direction during the paving operation, the measuring line moves slowly along a predetermined measuring field length, preferably starting from a rear edge of the screed, backwards through the temperature measuring field region opposite to the paving direction. It is conceivable that the temperature measuring field area could be scanned again and again using line scanning movements carried out at intervals in order to detect interfering objects positioned on the paving layer. A line sensor driven by a motor can be used for the line scanning movements.

In a preferred embodiment the use of an IR camera is intended, since with this several scanning lines can be put into a taken image.

A preferred embodiment provides that a motion sequence of at least one measuring line is controlled as a function of a paving process parameter, especially in view of the paving speed of the road finisher. In particular, it is conceivable that a scanning rate for a motion sequence of the measuring line could be controlled automatically, in particular in proportion to the paving speed of the road finisher, as a function of the recorded paving speed. The measuring line can pass through the measuring range at a scanning speed that is a multiple of the paving speed in order to reliably detect the presence of interfering objects.

It is also conceivable that, as a function of the detected paving speed of the road finisher, a predetermined, linked motion scheme for the measuring line is automatically called up, whereby the measuring process is optimally adapted to the paving mode of the road finisher.

An embodiment of the disclosure provides that along a plurality of measuring lines arranged behind each other transversely to the paving direction at a predetermined distance relative to a screed rear edge of the screed the respective temperatures of the measuring points arranged therein are detected simultaneously, for instance by means of an IR camera attached at the road finisher during paving of the paving layer. This enables a two-dimensional temperature detection behind the screed at the surface of the paving layer.

With regard to different types of road finishers, in particular different pave widths, it is particularly advantageous if a measuring line width running transversely to the direction of travel can be adjusted manually and/or automatically as a function of the paving width of the paving layer.

In practice, it may be advantageous if the nominal temperature range of at least one measuring point, especially for measuring points arranged in a measuring line, is adjusted as a function of the elapsed paving time. This can be done under consideration of a determined cooling coefficient of at least one adjacent measuring point. This makes it possible, even after a long period of time of an interfering object at the measuring point on the paving layer, to later retroactively bring a paving material temperature, which has already cooled down strongly there and was detected in view of a nominal temperature range originally defined for the measuring point, into connection with a interfering object-related faulty measurement, even after a longer period of time of an interfering object at the measuring point, whereupon the temperature value, which was originally incorrectly detected at the first point in time, could be corrected retrospectively. As the paving time increases, the nominal temperature range may tend to include lower temperature values than at previous times during paving.

Preferably, if an interfering object has been detected, a visual, acoustic and/or tactile signal is provided on the road finisher, on the interfering object itself and/or on another vehicle involved in the paving. This is to inform the operating personnel present at the paving site about the creation of the temperature field, and in particular that the detected interfering object is to be moved out of the temperature measuring range.

The disclosure also refers to a road finisher comprising a paving screed for laying a paving layer, a detection unit for establishing a temperature field of at least a portion of the paving layer in the laid condition behind the paving screed, and a control unit, which, based on measured values of the detection unit is configured to detect an interfering object which is positioned temporarily on the paving layer within at least one measuring range of the temperature field, whose intrinsic temperature is below a desired, nominal temperature range for the measuring range, so that an image of the intrinsic temperature of the interfering object in the temperature field to be generated falsifies the same at least in places.

According to the disclosure, the detection unit is designed to measure a temperature of at least one measuring point within the measuring range at different times in order to detect the interfering object. A characteristic feature of the road finisher according to the disclosure is that the control unit is configured to detect that, when the paving layer is being laid, the measuring point is covered by an interfering object at a first point in time if, contrary to an expected material-specific cooling at a later second time during paving at the same measuring point, a larger temperature value, in particular a temperature value lying within the nominal temperature range is measured than the temperature value detected at the preceding first time, and further configured to assign a new temperature value of the measuring point in the temperature field instead of the temperature value detected at the first time.

The road finisher according to the disclosure is therefore configured to correct temperature measurements retroactively for temperature measurements that are not plausible, i.e., temperature measurements that indicate an increase in temperature as a function of time at a measuring point of the paving layer, by means of a control process, so that these temperature measurements do not remain within the temperature field to be generated. As a result, a more precise overall temperature field can be produced, in particular for quality control purposes.

Temperature values detected in relation to an interfering object and therefore not reproducing the actual temperature value of a measuring point can be corrected with particular precision if the control unit is configured, when creating the temperature field for the paving layer, to use as the new temperature value for the measuring point the later, larger temperature value detected at the same measuring point, in particular taking into account a determined cooling coefficient of at least one adjacent measuring point.

To provide a reliable indication in the temperature field of material too coldly installed in the paving layer, the control unit is preferably designed, when creating the temperature field for the paving layer, to replace the temperature value detected at the first time by the new temperature value if the temperature value detected at the first time does not exceed a temperature threshold. Thus, for a temperature measurement field correction in the sense of the disclosure, only measuring points along the paving layer are actually considered at which temperatures of temporarily positioned interfering objects were detected, whereby actual paving material defects are mapped in the temperature field at points of the paving layer where temperatures above the temperature threshold and below the nominal temperature range are detected.

An advantageous embodiment provides that the detection unit has at least one IR camera which detects the temperature values of several measuring points along at least one measuring line running transversely to the paving direction within the measuring range.

An alternative embodiment provides that the detection unit has at least one line sensor which is configured to detect respective temperature values of a plurality of measuring points along at least one measuring line running transversely to the direction of paving within the measuring range, wherein the line sensor being mounted movably on the road finisher in such a way that, during a paving operation in the direction of paving, the at least one measuring line can be moved opposite to the direction of paving in order to detect the respective temperatures at the measuring points arranged therein at different points in time.

Embodiments according to the disclosure are explained in more detail using the attached drawings.

DETAILED DESCRIPTION

Figure 1:
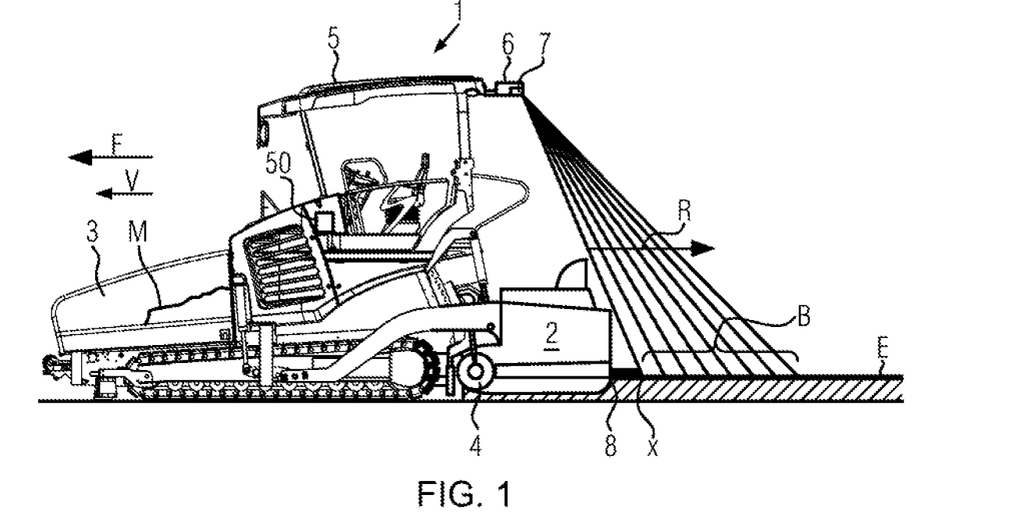
FIG. 1 shows a road finisher with a detection unit for creating a temperature field of at least one section of a newly laid paving layer behind the screed.

FIG. 1 shows a road finisher 1 for producing a paving layer E. The road finisher 1 has a paving screed 2 which is supplied with paving material M from a material hopper 3 by means of a longitudinal transport device, which is not shown, for paving the paving layer E. In front of paving screed 2, the paving material M transported to it is distributed by means of a spreading auger 4 according to a paving width.

A detection unit 6 for measuring the surface temperature profile of paving layer E is attached to the roof 5 of the road finisher 1. The detection unit 6 is equipped with a line sensor 7 or an IR camera 7', which is configured to detect the respective temperatures at measuring points x line by line, distributed over the paving width of the layer E, at least at intervals opposite to a paving direction F in a measurement direction R transverse to the paving direction F. The line sensor 7 can continuously scan a measuring range B line by line and recognize whether only nominal temperature values T are detected at the measuring points x in measuring range B or not. To measure the temperature distribution, a measuring line 10 (see FIG. 3A) can move slowly along a predetermined distance from a screed rear edge 8 in the measuring direction R in the opposite direction to the paving direction F in order to measure the temperature distribution in the measuring range B line by line.

Figure 2A:
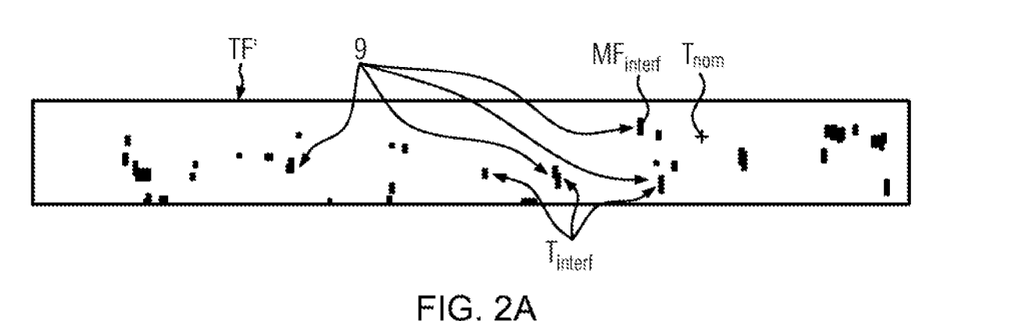
FIG. 2A shows a temperature field of a new paving layer including faulty interfering object measurements.

FIG. 2A shows a temperature field TF' in which interfering object-related measuring errors $MF_{interf}$ are imaged. FIG. 2A therefore refers in several places in the temperature field TF' to detected interfering objects 9 whose intrinsic temperature $T_{interf}$ is below a desired, nominal temperature range $T_{nom}$ for the measuring point x, so that the imaging of the intrinsic temperature $T_{interf}$ of the interfering objects 9 positioned and detected along the paving layer E at several places falsifies the temperature field TF' in accordance with FIG. 2A.

Figure 2B:
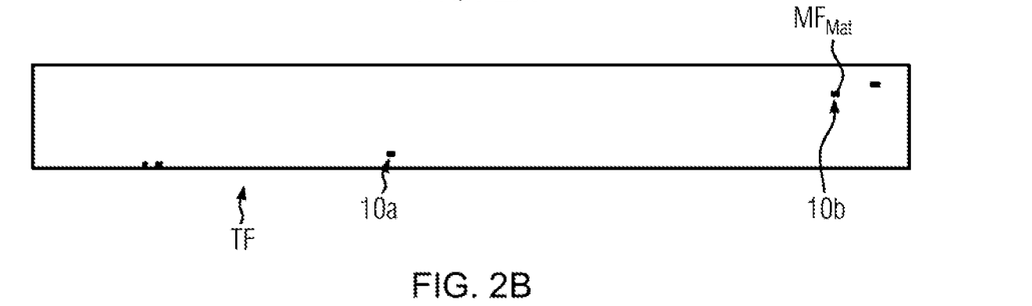
FIG. 2B shows a temperature field of a new paving layer adjusted for faulty measurements related to the interfering object according to the disclosure.

FIG. 2B shows a temperature field TF adjusted for the interfering objects shown in FIG. 2A, which can be achieved by means of a multiple measurement according to the disclosure. According to FIG. 2B, the temperature field TF is formed with a homogeneous temperature profile, whereby at only two measuring points 10a and 10b, material faulty measurements $MF_{Mat}$ are indicated at whose measuring points 10a, 10b actually too cold paving material M was laid. Interfering objects 9 according to FIG. 2A are no longer contained in the temperature field TF because they were filtered out or overwritten using the method according to the disclosure, so that the actual material quality of the paving layer E can be better assessed in qualitative terms.

Figure 3A:
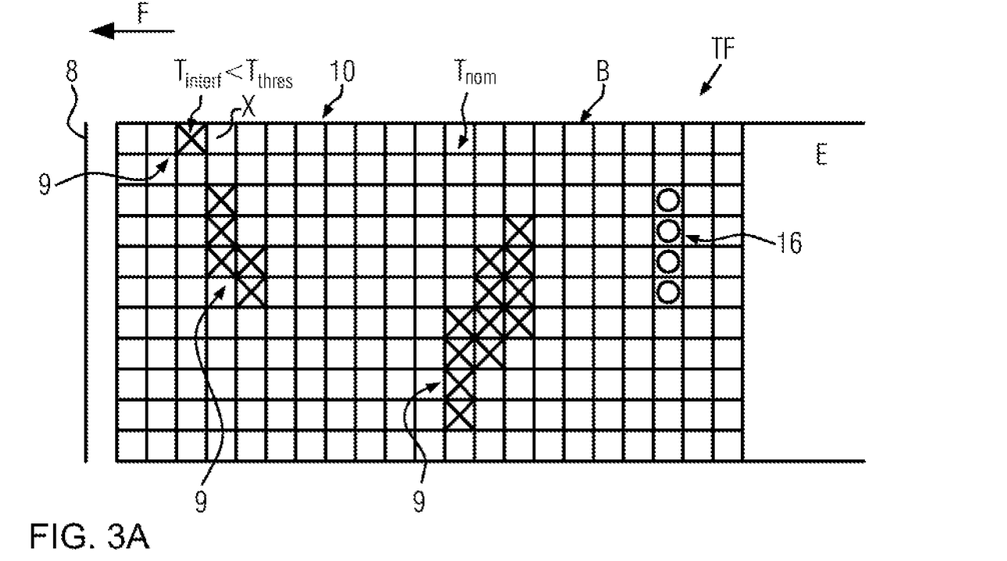
FIG. 3A shows a schematically represented temperature field with detected interfering objects.

FIG. 3A shows the measuring range B of the temperature field TF of the paving layer E. According to FIG. 3A, temperature values T detected at the respective measuring points x within the measuring range B are detected along a plurality of measuring lines 10 extending one behind the other transversely to the paving direction F.

At the measuring points x filled with a cross X, there are interfering objects 9 according to the respective snapshots according to FIG. 3A, which each have an intrinsic temperature $T_{interf}$ outside the nominal temperature range $T_{nom}$ and furthermore fall below a temperature threshold $T_{thres}$. An actual paving fault 16 is present at the measuring points x marked with a circle O in FIG. 3A. At these measuring points x too cold paving material M was used.

According to the disclosure, interfering objects 9 can be detected if, contrary to an expected material-specific cooling 11 (see FIG. 3B), at a later time $t_x$ (see FIG. 5) during the paving at the same measuring point x a temperature value T which is greater, in particular lying within the nominal temperature range $T_{nom}$, than a temperature value T detected at a preceding time $t_{x-1}$ at the same measuring point x, is measured, preferably with the proviso that the temperature T initially detected below the nominal temperature range $T_{nom}$ does not exceed a temperature threshold value $T_{thres}$.

Figure 3B:
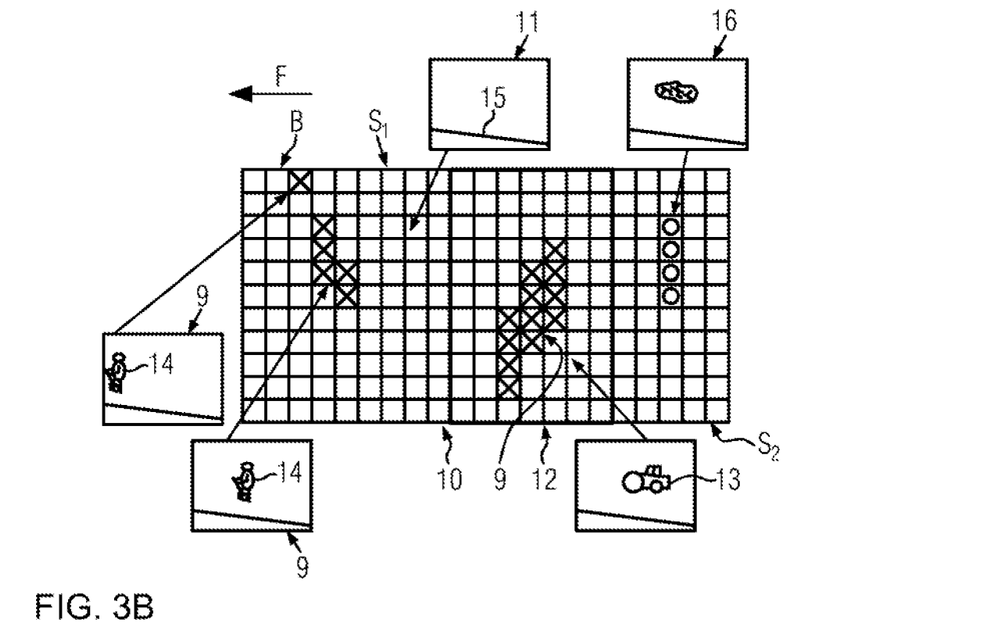
FIG. 3B shows a schematically represented temperature field with the interfering objects assigned to the respective faulty measurements.

FIG. 3B shows a schematic representation of possible interfering objects 9 along the measuring range B of the temperature field TF. In a thickly framed area 12 of measuring range B, temperatures T are measured at numerous measuring points x of three consecutive measuring lines 10 outside the temperature nominal range $T_{nom}$, which, according to FIG. 3B, indicate a compressor vehicle 13 following the road finisher 1, which moves on the paving layer E during a temperature measurement taking place there. In the paving direction F, at a point further in front of the measuring range B, persons 14 are detected on paving layer E. In the measuring range B between the persons 14 detected and the compressor vehicle 13 detected in the range 12, there is a homogeneous temperature distribution in four successive measuring lines 10 at the respective measuring points x of a measuring segment S1 in accordance with the desired, nominal temperature range $T_{nom}$. In the measuring segment S1 of the measuring range B, a material-specific cooling 11 is determined which reflects a cooling coefficient 15 of the paving material M.

In a rear measuring segment S2 of measuring range B, along the third-last measuring line 10 at four adjacent measuring points x paving error 16 are detected by detecting a material temperature at these measuring points x which is below the desired, nominal temperature range $T_{nom}$, but above the temperature threshold $T_{thres}$. Contrary to the interfering object-related measuring faults $MF_{interf}$, material fault measurements $MF_{Mat}$ indicate actual paving faults in the paving layer E and are consequently included in the production of the temperature field image TF (see FIG. 2B).

Figure 4:
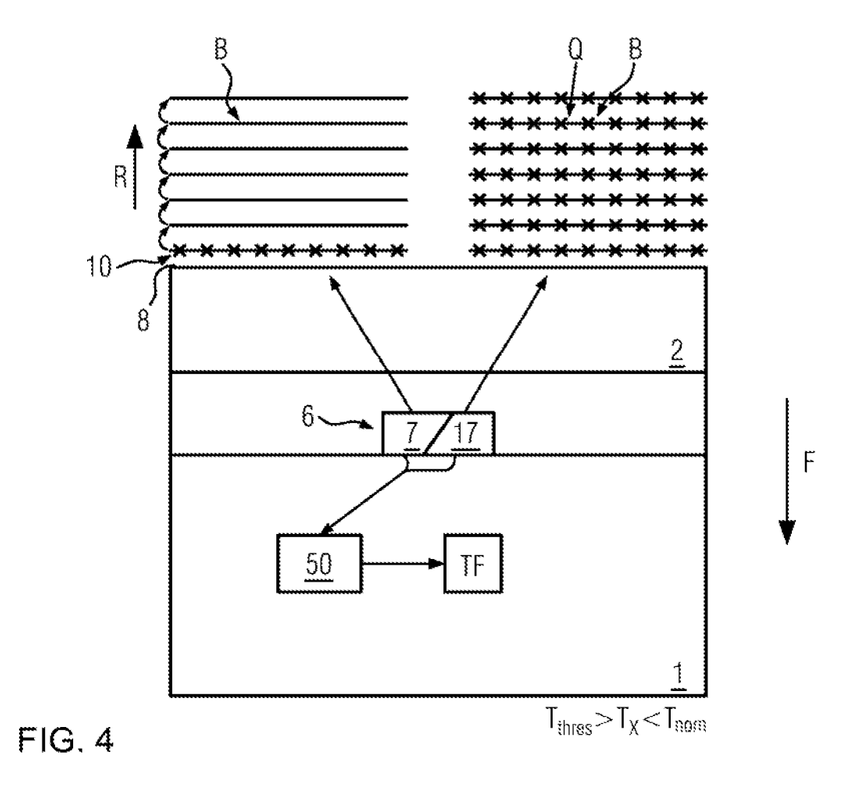
FIG. 4 shows a schematic representation of a line sensor movably mounted on the road finisher or of a surface sensor for detecting the temperature field of the paving layer.

FIG. 4 shows a schematic view of road finisher 1 with paving screed 2 from above. FIG. 4 shows a variant of road finisher 1 with a line sensor 7 and an alternative variant of road finisher 1 with a surface sensor 17. In accordance with FIG. 4, either a line sensor 7 or a surface sensor 17 is provided on road finisher 1 in order to detect the temperature distribution TF of the paving layer E.

During paving of paving layer E behind paving screed 2, the line sensor 7 detects the respective temperatures T at the measuring points x of a measuring line 10, which during paving is slowly moved away from the rear edge 8 of the screed 2 in the measuring direction R, in the opposite direction to the paving direction F. Moving the measuring line 10 backwards line by line at several recurring intervals opposite to the paving direction F enables the respective temperatures T of several measuring points x lying along the measuring line 10 to be sampled several times, whereby interfering objects 9 can be detected within the measuring range B.

By means of the area sensor 17 schematically shown in FIG. 4, the respective temperatures T occurring in the measuring range B at the different measuring points x can be detected over the entire area, i.e., along several measuring lines 10 simultaneously. According to FIG. 4, the two-dimensional measuring surface Q spanned by the area sensor 17 corresponds to the entire measuring range B, but can also be smaller.

The respective temperature values T detected by the detection unit 6 are fed to a control unit 50 of the road finisher 1. The control unit 50 is configured to generate the temperature field TF according to FIG. 2B, which is corrected for the interfering object related temperature measurements $MF_{interf}$.

Figure 5:
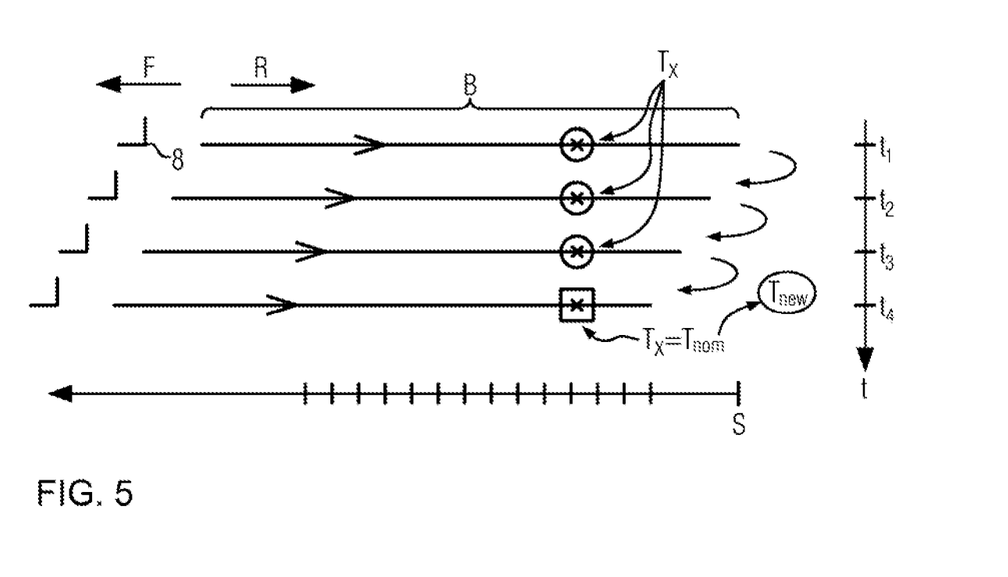
FIG. 5 shows a schematically represented line scan sequence for producing the measuring point temperature at different times.

FIG. 5 shows a schematic representation of a chronological sequence of the measurement of a temperature $T_x$ at a measuring point x at different times $t_1$ to $t_4$ along the paving section S.

At the times $t_1$ to $t_3$, it is indicated by means of the respective measurement point x displayed in a circle that the temperature values $T_x$ detected at the measurement point x during paving belong to a interfering object 9, because the respective temperature values $T_x$ at the measurement point x are smaller than the desired, nominal temperature range $T_{nom}$ and also smaller than a temperature threshold $T_{thres}$.

At time $t_4$ the interfering object 9 has left the measuring point x so that, as indicated by a box at measuring point x, there is now a temperature value $T_x$ which is the nominal value. If the intrinsic temperature $T_{interf}$ of the interfering object 9 has been mapped in the temperature field TF, the measuring point x can now be assigned a new temperature value $T_{new}$, which corresponds to the temperature value $T_x$ at the time $t_4$, if necessary corrected on the basis of the determined cooling coefficient 15 (see FIG. 3B) of at least one adjacent measuring point x. The new temperature value $T_{new}$ is then used to overwrite the original interfering object related temperature value $T_x$ in the TF temperature field.

Figure 6:
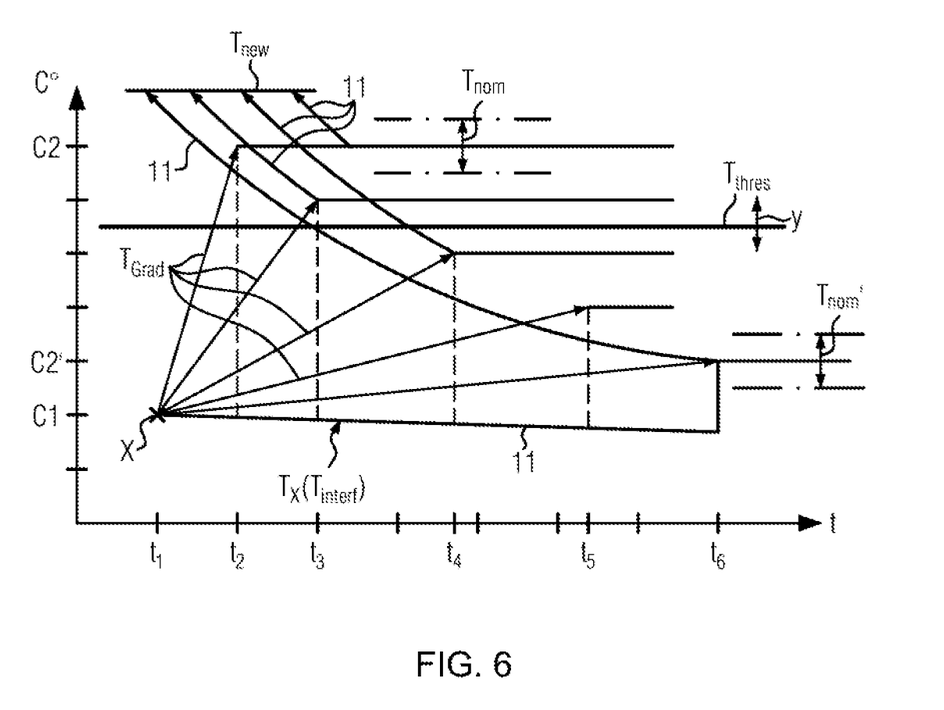
FIG. 6 shows a schematic representation of a temperature gradient curve at a measuring point as an indication of an interfering object.

FIG. 6 schematically shows the detected temperature value $T_x$ at a predetermined measuring point x over time t. At time $t_1$, a temperature C1 is detected at measuring point x. The temperature C1 is outside the nominal temperature range $T_{nom}$ and below the temperature threshold $T_{thres}$. FIG. 6 also shows that the temperature value $T_x$ decreases over time $t_1$ to $t_6$ due to material-specific cooling.

In addition, FIG. 6 shows a plurality of temperature gradients $T_{Grad}$, which generally indicate an interfering object detection. For example, the measuring point x covered by the interfering object 9 at time t1 is released at time t2, i.e., the interfering object 9 no longer covers the measuring point x at time t2, so that at time t2 the temperature C2 at the measuring point x is detected instead of the intrinsic temperature $T_{interf}$(C1) detected at time t1. According to FIG. 6, the temperature C2 is in the nominal temperature range $T_{nom}$ and can be converted into a new temperature value $T_{new}$, preferably taking into account the cooling coefficient 11 of an adjacent measuring point x or with the aid of a predetermined material-specific cooling coefficient, which is then used in the temperature field TF at measuring point x by means of the control 50.

If the interference object 9 remains at the measuring point x for a longer period of time, e.g., until time t6, the temperature C2' is detected according to FIG. 6 when the measuring point x is released, which lies within a nominal temperature range $T_{nom}$, adjusted as a function of time. The new temperature value $T_{new}$ can also be derived at time t6 using the cooling coefficient 11 as shown in FIG. 6, so that even after the interfering object 9 has stayed at the measuring point x for a long time, the new temperature value $T_{new}$ is used for the measuring point x in the temperature field TF.

According to FIG. 6, the temperature threshold $T_{thres}$ may be adjustable (displacement y), preferably with respect to the elapsed time t. This can be done, for example, proportionally to an adjustment of the nominal temperature range $T_{nom}$.

Figure 7:
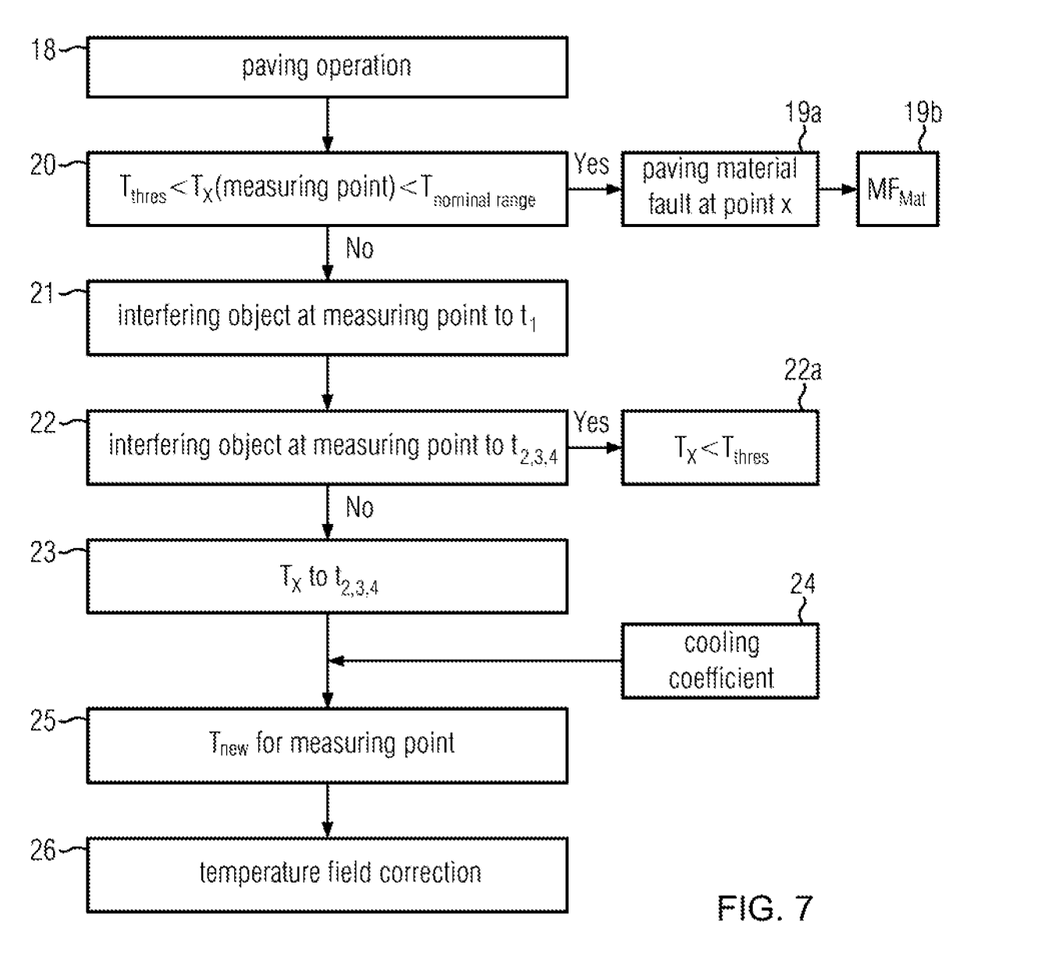
FIG. 7 shows a schematic representation of a method according to the disclosure.

FIG. 7 shows a schematic representation of a method according to the disclosure. In a first method step, road finisher 1 is in a paving operation 18. During paving operation 18 the road finisher 1 is paving the paving layer E. The road finisher 1 moves slowly forwards in paving direction F, while the measuring line 10 moves slowly away from the rear edge 8 of the screed 2 towards the rear in measuring direction R in order to perform a multiple measurement of the temperature distribution in the measuring range B. Alternatively, an area measurement according to FIG. 4 is possible.

At measuring points x within measuring range B, temperature measurements are now carried out several times using the following process steps in order to find out whether measuring points x of measuring range B are temporarily occupied by interfering objects 9, so that the temperature field TF can be corrected accordingly if the answer is in the affirmative.

If temperature values T below a desired temperature range $T_{nom}$, but above a temperature threshold $T_{thres}$, are detected by means of temperature measurement, it is determined in method step 19*a* that paving material faults are present at the relevant measuring points x, which are mapped in the temperature field TF according to method step 19*b*. If, however, the measured temperatures are not nominal and are below the temperature threshold value $T_{thres}$, it is determined in accordance with method step 21 that a interfering object 9 is positioned at the corresponding measuring points x.

If at a later point in time $t_{2,3,4}$ in step 22 it is detected that the interfering object-related temperature $T_{interf}$ is no longer present, but that contrary to a material-specific cooling 11 a larger temperature $T_x$ is now present at the measuring point x (step 23), it is derived from this that the interfering object 9 is no longer positioned at the measuring point x.

The current temperature $T_x$ of the measuring point x at time $t_{2,3,4}$ is then recorded and corrected if necessary using the cooling coefficient 11 (step 24) in the temperature field TF as the new temperature $T_{new}$ (step 25) for the measuring point x (step 26).

What is claimed is:

1. A method for creating a temperature field of at least one section of a paving layer laid by means of a paving screed of a road finisher, the method comprising:

detecting an interfering object temporarily positioned on the laid paving layer within a predetermined measuring range of the temperature field, an intrinsic temperature of which being below a desired nominal temperature range for the measuring range, so that an imaging of the intrinsic temperature of the interfering object in the temperature field to be generated falsifies the same at least in places, wherein for detecting the interfering object a temperature of a measuring point lying within the measuring range is measured at different times, wherein it is detected that during the paving of the paving layer, the measuring point is covered by the interfering object at a first time if, contrary to an expected material-specific cooling at a later second time during the paving, at the same measuring point a larger temperature value lying within the nominal temperature range than a temperature value detected with respect to the preceding first time is measured, wherein instead of the temperature value detected at the first time a new temperature value of the measuring point is assigned in the temperature field.

2. The method according to claim 1, wherein, when the temperature field is created for the paving layer, the temperature value detected at the first time is replaced by the new temperature value if the temperature value detected at the first time does not exceed a temperature threshold value.

3. The method according to claim 1, wherein the nominal temperature range at the measuring point is adapted for different times taking into account a determined cooling coefficient of at least one adjacent measuring point.

4. The method according to claim 1, further comprising, upon detection of the interfering object, emitting a visual, acoustic and/or haptic signal on the road finisher, on the interfering object itself and/or on another vehicle involved in the paving.

5. The method according to claim 1, wherein for detecting the interfering object an object detection in an evaluation software is used.

6. The method according to claim 5, wherein for detecting the interfering object it is checked in the evaluation software whether interfering objects move relative to the paving speed.

7. The method according to claim 1, wherein, when creating the temperature field for the paving layer, the later larger temperature value detected at the same measuring point is used as the new temperature value for the measuring point.

8. The method according to claim 7, wherein the later larger temperature value detected at the same measuring point is corrected taking into account a determined cooling coefficient of at least one adjacent measuring point before the new temperature value thus obtained replaces the temperature value detected at the first time.

9. The method according to claim 1, wherein respective temperature values of a plurality of measuring points are detected along at least one measuring line running transversely to the paving direction within the measuring range.

10. The method according to claim 9, wherein along a plurality of measuring lines arranged one behind the other transversely to the paving direction at a predetermined distance relative to a screed rear edge of the paving screed, the respective temperatures of the measuring points arranged therein are detected simultaneously during the paving of the paving layer.

11. The method according to claim 9, wherein a respective measuring line width is adapted with respect to a paving width of the paving layer.

12. The method according to claim 9, wherein the at least one measuring line is moved at different times at least temporarily opposite to the paving direction during the paving of the paving layer for detecting the respective temperatures at measuring points arranged therein.

13. The method according to claim 12, wherein a motion sequence of at least one measuring line is set as a function of a paving speed of the road finisher.

14. A road finisher comprising:
a paving screed for laying a paving layer;
a detection unit for creating a temperature field of at least a portion of the paving layer in a laid state behind the paving screed; and
a control unit which, based on measured values of the detection unit, is configured to detect an interfering object positioned temporarily on the paving layer within at least one predetermined measuring range of the temperature field, whose intrinsic temperature lies below a desired, nominal temperature range for the measuring range so that a mapping of the intrinsic temperature of the interfering object at least in places falsifies the temperature field to be generated;
wherein the detection unit is adapted for detecting the interfering object to measure a temperature of at least one measuring point lying within the measuring range at different times, wherein the control unit is configured to detect that, when the paving layer is paved, the measuring point is covered by an interfering object at a first time, if, contrary to an expected material-specific cooling at a later second time during paving at the same measuring point, a larger temperature value lying within the nominal temperature range than a temperature value measured at the preceding first time is measured, and is further configured to assign a new temperature value to the measuring point in the temperature field instead of the temperature value detected at the first time.

15. The road finisher according to claim 14, wherein the control unit is configured, when the temperature field for the paving layer is created, to use, as a new temperature value for the measuring point, the later larger temperature value recorded at the same measuring point.

16. The road finisher according to claim 14, wherein the control unit is configured, when the temperature field for the paving layer is created, to use, as a new temperature value for the measuring point, the later larger temperature value recorded at the same measuring point with inclusion of a determined cooling coefficient of at least one adjacent measuring point.

17. Road finisher according to claim 14, wherein the control unit is configured, when the temperature field for the paving layer is created, to replace the temperature value detected at the first time by the new temperature value, if the temperature value detected at the first time does not exceed a temperature threshold value.

18. The road finisher according to claim 14, wherein the detection unit has at least one line sensor which is designed to detect respective temperature values of a plurality of measuring points along at least one measuring line running transversely to a direction of paving within the measuring range, the line sensor being mounted movably on a portion of the road finisher in such a way that the at least one measuring line can be moved at different times at least temporarily in an opposite direction to the paving direction during a paving operation for detecting the respective temperatures at the measuring points arranged therein.

19. The road finisher according to claim 14, wherein the detection unit has at least one infrared camera which is configured to detect temperature values at a plurality of measuring points along at least one measuring line running transversely to a direction of paving within the measuring range.

* * * * *